United States Patent [19]

Gibson

[11] 4,331,028
[45] May 25, 1982

[54] METHOD AND APPARATUS FOR DETERMINING THE SHARPNESS OF A SAW CHAIN

[75] Inventor: Duane M. Gibson, Milwaukie, Oreg.

[73] Assignee: Omark Industries, Inc., Portland, Oreg.

[21] Appl. No.: 166,612

[22] Filed: Jul. 7, 1980

[51] Int. Cl.³ .............................................. G01N 15/00
[52] U.S. Cl. .................................... 73/104; 73/432 PS
[58] Field of Search .............. 73/104, 432 PS; D7/47; 209/235, 374, 397

[56] References Cited

U.S. PATENT DOCUMENTS

| | | | |
|---|---|---|---|
| 789,517 | 5/1905 | Williamson | D7/47 |
| 2,987,670 | 6/1961 | Derby et al. | 73/104 X |
| 3,729,096 | 4/1973 | Fitzner et al. | 209/374 |

Primary Examiner—James J. Gill
Attorney, Agent, or Firm—Klarquist, Sparkman, Campbell, Leigh, Whinston & Dellett

[57] ABSTRACT

A rectangular container for a saw chain is provided with a transparent plastic lid and a foraminous bottom. Freshly sawn wood chips are placed in the container after which a movable slide is located adjacent the level of the chips. After shaking of the container, a predetermined reduction in chip level as measured by the slide will indicate that the saw chain requires servicing.

20 Claims, 8 Drawing Figures

U.S. Patent  May 25, 1982  Sheet 1 of 2  4,331,028
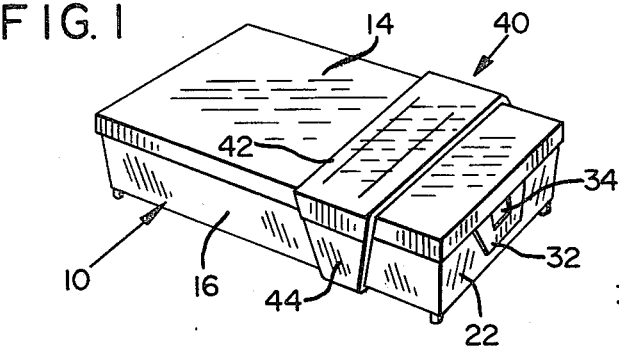
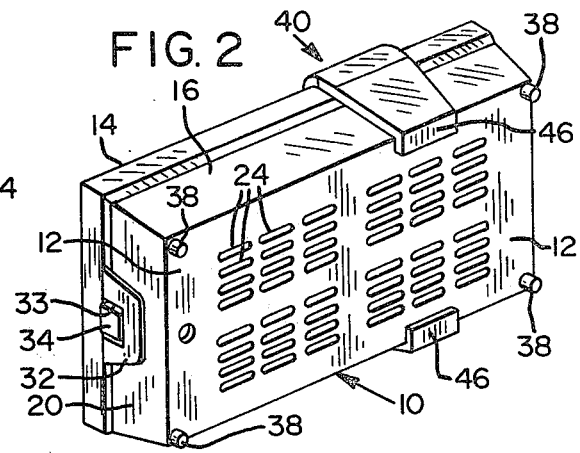
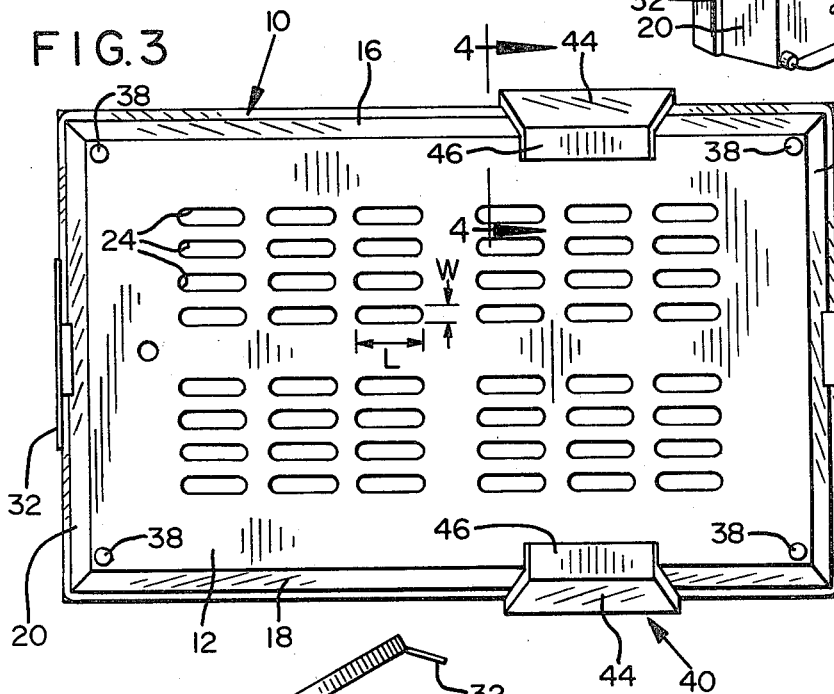
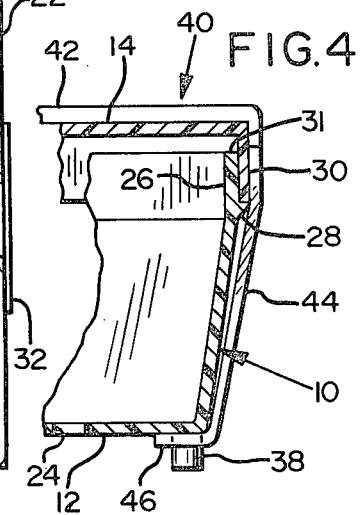
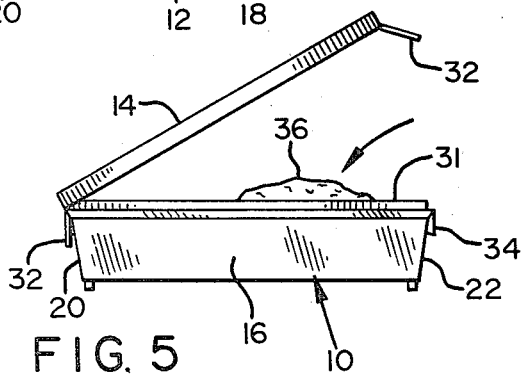
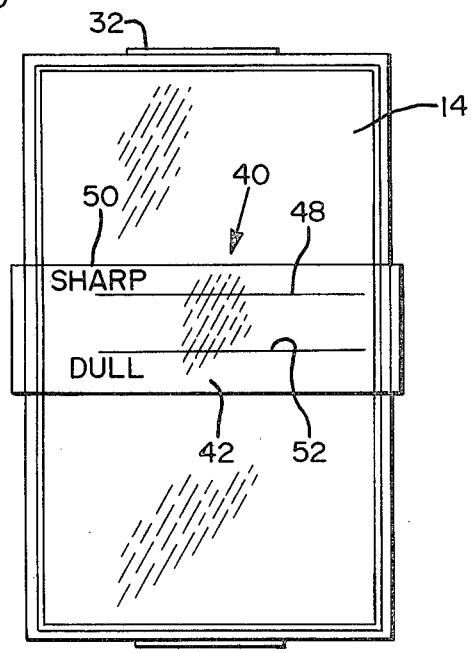

METHOD AND APPARATUS FOR DETERMINING THE SHARPNESS OF A SAW CHAIN

BACKGROUND OF THE INVENTION

The present invention relates to an improved method and apparatus for determining the sharpness of a saw chain and particularly to such a method and apparatus which can be readily utilized by the non-professional.

At one time the use of chain saws was more or less restricted to professional loggers, but more recently equipment of this type has become popular with the consuming public. For this reason, difficulties are sometimes encountered in maintaining the saw in proper and safe working order. While a "professional" may be able to detect an improperly operating chain from "feel," or the time required to perform a particular job, or from the general nature of the wood chips generated as the saw is utilized, one basically unfamiliar with saw chain operation usually lacks a standard by which to measure the efficiency of operation. Moreover, a method or apparatus is lacking for economically providing a quantitative measure of saw chain efficiency or sharpness.

SUMMARY OF THE INVENTION

According to the present invention, the sharpness of a saw chain is determined by operating the saw chain and collecting a quantity of wood chips produced. The wood chips are placed in a perforated, hand held container having a plurality of openings which are small enough to pass wood chips as would be generated by a dull or improperly sharpened chain. The container is shaken and the quantity of wood chips remaining in the container compared with those shaken out indicates the "dullness" of the chain. The container employed for measuring chain sharpness is suitably the same container used for shipping the saw chain and for storing the saw chain when not in use.

The aforementioned container is preferably provided with a measuring slide movable with respect to the container and having a cross member for aligning with the level of wood chips placed in the container. The container is shaken by hand for displacing a quantity of wood chips through the aforementioned openings as produced by a dull or improperly sharpened saw chain, with the reduction in wood chips within the container as measured by the slide being indicative of the relative dullness or sharpness of the chain.

It is accordingly an object of the present invention to provide an improved method and apparatus for ascertaining the sharpness of a saw chain.

It is another object of the present invention to provide an economical method and apparatus for quantitatively measuring the sharpness of a saw chain.

It is another object of the present invention to provide an improved method and apparatus for measurement of the sharpness of a saw chain by one who is a non-professional user.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 1 is a perspective view of a container according to the present invention employed for measuring the sharpness of a saw chain;

FIG. 2 is a perspective view of the FIG. 1 container, viewing the underside thereof;

FIG. 3 is a bottom view of the FIG. 1 container;

FIG. 4 is a cross-sectional view, partially broken away, as taken at 4—4 in FIG. 3;

FIG. 5 is a side view of the container according to the present invention showing the lid upraised for reception of a quantity of wood chips;

FIG. 6 is an elevational view of a container according to the present invention as turned on one end;

DETAILED DESCRIPTION

Figure 7:
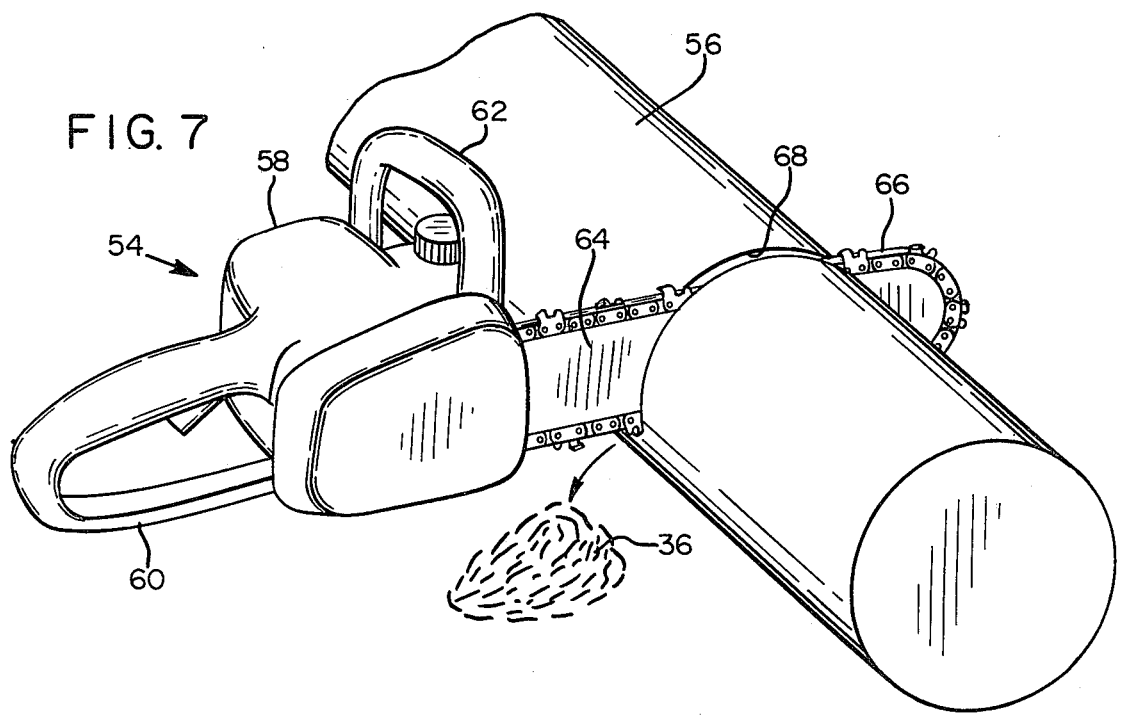
FIG. 7 illustrates the production of wood chips during the operation of a chain saw.

Referring to the drawings, and particularly to FIGS. 1 through 6, a container according to the present invention is in the form of a generally rectangular box 10 having six sides including a flat bottom 12 and a flat removable top closure or lid 14. The container is longer than it is wide having two long side walls 16 and 18, and two short side walls or ends 20 and 22, each of the side walls generally tapering inwardly from top to bottom such that the rectangular bottom 12 of the container is somewhat smaller in dimension than the top. The container is suitably formed of plastic and is hand holdable, the illustrated embodiment being approximately five inches long by three inches wide, and having a height of one inch. FIG. 3 of the drawings is drawn approximately to scale.

The tapered sidewalls are provided at their upper ends with a vertically upstanding edge or ridge 26 and an outwardly extending tapered flange 28, with the rim or side edges 30 of rectangular lid 40 being matingly receivable over edge 26 and against flange 28. The lid 14 is thus employed to cover the top opening 31 of the container but the lid is transparent so that the disposition of wood chips within the container can be visually observed. Lift tabs 32 located at each end of lid 14 are flexibly joined to the lid so as to be hingeable with respect to the lower rim of the lid. Each tab has a rectangular hole 33 for matingly receiving a rectangular boss 34 extending outwardly from end walls 20 and 22 of the container just below the location of the lid. The bosses are tapered slightly downwardly at their bottom edges such that tabs 32 can snap thereunder and secure the lid 14 in place on the container. To remove the lid, i.e. for the purpose of placing a quantity of wood chips 36 therewithin via opening 31 (as illustrated in FIG. 5), one or both of the tabs 32 are rotated outwardly. The bottom of the container is further provided with cylindrical feet 38 at the four corners of the bottom 12.

In practice, the container fulfills a dual purpose. Initially, the container provides a shipping box for a saw chain, and of course may be subsequently used for storing the saw chain. It is also utilized according to the present invention for determining the sharpness of the saw chain as gauged by dispersal of wood chips through the foraminous bottom 12 of the container. For either purpose, the lid 14 is desirably clear plastic material while the side walls and bottom need not be clear. The bottom 12 is provided with a plurality of elongated openings 24 suitably arrayed in rows extending crossways of bottom 12 with the direction of elongation of the openings being disposed longitudinally of the container. In the particular example illustrated, there are six rows of six openings each in order to provide an extensively foraminous or screenlike bottom for the container, but it is understood that a greater or somewhat lesser number of openings could be used.

The openings 24 are provided for the purpose of selectively passing wood chips therethrough and therefore the opening dimensions are related to those of wood chips sawn by a saw chain. The length, L, (FIG. 3) is related to the kerf width cut by the saw chain under investigation. In the case of the openings 24 illustrated in the drawings, the length, L, is approximately 0.4 inches in order to pass wood chips from a kerf having a width in the range of about 0.25 inches to 0.30 inches. The length L should be long enough to have a greater dimension than the kerf width, but should not be excessively long, i.e. it should not be more than about twice the width of the kerf. The width, W, of the openings 24 should be between 0.1 inches and 0.2 inches, with approximately 0.125 inches being suitable for conveniently measuring the sharpness of a saw chain. With openings having a width of 0.125 inches, a substantial proportion of the wood chips cut by a saw chain will pass through the openings 24 if the saw chain is dull. As hereinafter more fully indicated, for a 0.125 opening width the level of wood chips in container 10 will drop by approximately one-half inch when the container is shaken, if the chips are produced by a saw chain taking about twice as long to cut through a twelve inch log as would a sharpened chain. Of course, the level may drop a little faster for slightly wider openings or not as fast for narrower openings, but the range of opening width from the 0.1 inches to 0.2 inches has been found suitable in readily distinguishing between sharp and dull chains. The teeth of a properly sharpened saw chain will produce longer ribbon-like chips, but as the teeth become dull with use and need sharpening, the chips break off, becoming shorter and shorter until they fall in the 0.1 to 0.2 inch range. If the chain is properly sharpened, the chips will, for the most part, be unable to pass through the openings, and the drop in level after shaking will be insubstantial.

The container is further provided with a removable measuring slide 40 adapted to be received over the container between the ends thereof. The slide includes a cross member 42 extending crossways of the container, i.e. over the transparent lid 14 when the lid is positioned in place. Side arms 44 of the slide are disposed downwardly from cross member 42 along the side walls 16 and 18 of the container for guiding the slide in movement along the container. The side arms conclude in inwardly directed tabs 46 located immediately under the flat bottom 12 of the container for securing the slide to the container while extending insufficiently far to cover any of the openings 24. The tabs 46 do extend past the positions of feet 38 whereby the feet prevent the slide, when in place, from inadvertently moving off the end of the container. The feet are also long enough to support the container horizontally despite the presence of tabs 46 thereunder. It will be observed the arms 44 of the measuring slide are trapezoidal in side elevation and are also bent to extend first along the rim 30 of the lid, and then taper inwardly along tapered side walls 16 and 18 of the container. The slide 40 is desirably formed of transparent plastic, and is flexible to the extent that arms 44 can be drawn apart slightly to snap the slide over the container from the top or from the end with the lid 14 in place.

The cross member of the slide is suitably provided with markings indicated in FIG. 6, namely the word "SHARP" followed by a horizontal line 48 positioned about one-quarter inch below forward edge 50 of the cross member, and a further horizontal line 52 parallel to line 48 and spaced about one-half inch therefrom. The word "DULL" is located immediately under line 52. As further indicated hereinafter, the slide is positioned along the container with line 48 proximate the level of wood chips in the container. After shaking the container if the level of chips drops substantially, i.e. to the level of line 52 or below, it is an indication that the chips were produced by a dull saw chain. For a container about two-thirds to three-fourths full of wood chips and having the approximate dimensions given, i.e. five inches by three inches by one inch, the difference in volume represented between the "SHARP" line 48 and the "DULL" line 52 is about twelve to fifteen percent. That is a twelve to fifteen percent reduction in the quantity of wood chips within the container would have taken place as the result of shaking.

FIG. 7 depicts a chain saw 54 for cutting a wooden log or other workpiece 56. The chain saw comprises a frame 54 including a motor housing and handles 60 and 62, and supports a forwardly extending saw bar 64 having a saw chain 66 entrained therearound. In cutting the workpiece in conventional fashion, wood chips 36 are produced which are employed according to the present invention for determining the sharpness of the chain 66. The width of the chips is comparable to the width of saw kerf 68, with the openings 24 of the container 10 having a length, L, slightly longer than the kerf width as hereinbefore mentioned.

Figure 8:
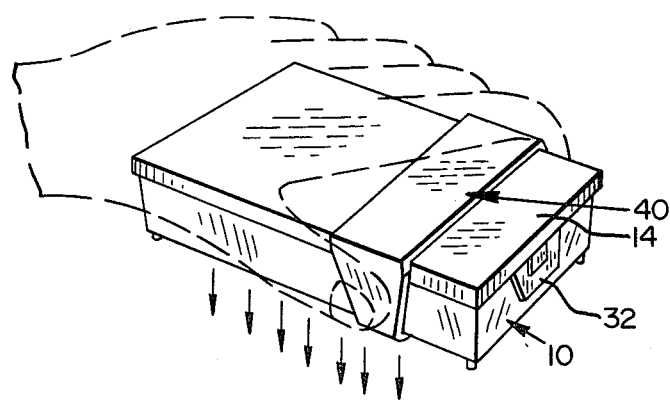
FIG. 8 illustrates a step according to the method of the present invention of shaking wood chips through openings in the aforementioned container.

After producing the wood chips 36 with saw chain 66 of undetermined sharpness, container 10 is opened as illustrated in FIG. 5 for the reception of a quantity of the freshly cut wood chips therewithin. The container is filled approximately two-thirds to three-fourths full, with the wood chips disposed loosely therein so there is no packing or binding between the chips and the container. The lid 14 is closed and secured by means of tabs 32, after which the measuring slide 40 is snapped over the sides of the container. The container is then turned on one end as illustrated in FIG. 6, i.e. with its longer direction vertical so the wood chips located therewithin fall toward the downwardly projecting end. The slide 40 is positioned as illustrated in FIG. 6 with the "SHARP" line 48 disposed adjacent the top of the level of the chips. The container is hand held, disposed horizontally as illustrated in FIG. 8, and shaken vigorously fifteen to twenty times substantially in the lateral direction, i.e. in the direction lengthways of slide 40 or crossways of container 10. The slide 40 is kept in exactly the same position by holding it with the container as illustrated in FIG. 8, i.e. by compression toward the container. As the container is shaken, the smaller chips will fall through the openings in the bottom of the container, with the container providing a screening action. The container is then held upright again, in the same manner as illustrated in FIG. 6, and the level of the chips relative to slide 40 and particularly relative to the gauge lines 48 and 52 is observed. If the level of the chips has not dropped significantly below line 48, the saw chain may be considered sharp and usable, but if the level of chips has fallen near or below the "DULL" line 52, the chain 66 will require resharpening. A significant proportion of wood chips will thus pass through the container perforations for chips produced by dull saw teeth, while chips produced by sharp saw teeth are longer and more ribbon-like that will not pass through the openings. The method determines the overall sharpness of the saw chain employed.

As mentioned, a drop in level from line 48 to line 52, spaced one-half inch therebelow, indicates a saw chain that would take about twice as long to cut through a twelve inch log, such as illustrated at 56 in FIG. 7, as would a sharpened chain, premised upon the width, W, of the openings 24 being approximately 0.125 inches. For a sharpened chain 66, approximately six seconds should be taken in cutting through a twelve inch Douglas fir log. If the saw chain is sufficiently dull that the level of wood chips in the container drops by about one-half inch, the chain will take eight to ten seconds or more to cut through the same log.

Of course, it is desirable to keep a chain properly sharpened since the sharpened chain will cut more quickly, more smoothly and will save fuel. Dull chains can also increase saw bar damage and engine wear. However, it will be observed that the present method does not require judgment or expertise as to the proper appearance or feel of the saw chain in operation. Neither is the cutting of a standard log required, nor indeed a knowledge of how rapidly a saw chain should saw through a standard log. Therefore, the sharpness of a saw chain can be easily ascertained by any saw chain user.

While I have shown and described preferred embodiments of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. A hand holdable container adapted for ascertaining the sharpness of a saw, said container including an opening for reception of a quantity of freshly sawn wood chips therewithin and a removable closure for said opening, a portion of said container being foraminous having a plurality of elongated openings each having a length greater than the width of the kerf cut by said saw and a width insufficient to pass the length of the majority of ribbon-like chips cut by sharp saw teeth while passing a proportion of chips cut by dull saw teeth as a result of said chips being shorter than the width of the elongated opening, the remainder of the container cooperating to form an enclosure for said chips adapting the container to be hand manipulated for shaking smaller wood chips through said plurality of openings such that the quantity of larger wood chips remaining compared with the quantity of freshly sawn wood chips as initially received in said container indicates the overall sharpness of the saw.

2. The container according to claim 1 wherein said container is at least partially transparent so that the disposition of wood chips therewithin can be visually observed.

3. A hand holdable container adapted for ascertaining the sharpness of a saw, said container including an opening for reception of a quantity of freshly sawn wood chips therewithin and a removable closure for said opening, a portion of said container being foraminous having a plurality of small openings each having a size smaller than the majority of individual wood chips cut by a properly operating and sharpened saw tooth, and the size of each of the openings being larger than at least a proportion of wood chips cut by an improperly operating or dull saw tooth so that the last mentioned chips can pass through said openings while the majority of the chips cut by a properly functioning saw tooth cannot, the remainder of the container cooperating to form an enclosure for said chips adapting the container to the hand manipulated for shaking smaller wood chips through said plurality of openings such that the quantity of larger wood chips remaining compared with the quantity of freshly sawn wood chips as initially received in said container indicates the overall sharpness of the saw, and further including a measuring slide movable along said container for initial positioning adjacent the level of wood chips initially placed within said container so that the reduction in quantity of wood chips in said container by shaking thereof can be readily ascertained.

4. A hand holdable container adapted for ascertaining the sharpness of a saw, said container being rectangular in shape and including an opening for reception of a quantity of freshly sawn wood chips therewithin and a removable closure for said opening comprising a lid, said container having a substantially flat bottom which is foraminous having a plurality of small openings each having a size smaller than the majority of individual wood chips cut by a properly operating and sharpened saw tooth, and the size of each of the openings being larger than at least a proportion of wood chips cut by an improperly operating or dull saw tooth so that the last mentioned chips can pass through said openings while the majority of the chips cut by a properly functioning saw cannot, the remainder of the container cooperating to form an enclosure for said chips adapting the container to be hand manipulated for shaking smaller wood chips through said plurality of openings such that the quantity of larger wood chips remaining compared with the quantity of freshly sawn wood chips as initially received in said container indicates the overall sharpness of the saw, said container being at least partially transparent so that the disposition of wood chips therewithin can be visually observed, at least said lid being transparent, and further including a measuring slide movable along said container and received over said transparent lid for initial positioning adjacent a level of wood chips initially placed within said container so that the reduction in quantity of wood chips in said container by shaking thereof can be readily ascertained.

5. A hand holdable container adapted for shipping or storing a saw chain, one side of said container including an opening for removal of said saw chain and providing for reception of freshly sawn wood chips into said container and a closure for said opening adapted to be secured against said opening, at least one side of said container being foraminous including a plurality of elongated openings having a length greater than the width of the kerf cut by said saw chain and a width between about 0.1 inches and 0.2 inches such that the last mentioned width is insufficient to pass the length of the majority of the ribbon-like chips cut by sharp saw teeth while passing a proportion of chips cut by dull saw teeth as a result of said chips being shorter than the width of an elongated opening, the remainder of the container cooperating to form an enclosure for said chips adapting the container to be hand manipulated for shaking smaller wood chips through said plurality of openings, said container being at least partially transparent so that the disposition of wood chips therewithin can be visually observed.

6. The container according to claim 5 wherein said container comprises a rectangular box, said foraminous side comprising a substantially flat bottom of said box.

7. The container according to claim 6 wherein said side including an opening and a closure comprises the top of said rectangular box provided with a rectangular lid.

8. The container according to claim 7 wherein said container including said lid is formed of plastic.

9. The container according to claim 7 wherein ends of said lid are provided with hingeable tabs each having an aperture, the ends of said container below said lid being provided with bosses receivable in said apertures for securing said lid in place.

10. A hand holdable container adapted for shipping or storing a saw chain, said container being rectangular and one side of said container including an opening for removal of said saw chain and providing for reception of freshly sawn wood chips into said container and a closure for said opening adapted to be secured against said opening, at least one side of said container being foraminous including a plurality of small openings having a size smaller than the majority of individual wood chips as cut by a properly operating saw so that the majority of chips from a properly operating saw will fail to pass therethrough, said plurality of openings being sufficiently large to pass a quantity of small sized wood chips as cut by a dull or improperly operating saw, the remainder of the container cooperating to form an enclosure for said chips adapting the container to be hand manipulated for shaking smaller wood chips through said plurality of openings, said container being at least partially transparent so that the disposition of wood chips therewithin can be visually observed, said container being provided with a measuring slide received in slidable relation along said container substantially between ends of said container, said slide having a cross member extending crossways of said container over the at least partially transparent portion thereof, adapting said slide to be positioned adjacent the level of said wood chips within said container prior to shaking thereof, for ascertaining the quantity of wood chips within said container before and after shaking of said container.

11. The container according to claim 10 wherein said container is longer in the direction of movement of said slide and narrower in the direction of said cross member so that said container is suitably oriented with its longer direction vertical and the wood chips located toward one end for positioning of said slide adjacent the top of the level of wood chips within said container.

12. The container according to claim 11 wherein said smaller openings are elongated and disposed in multiple aligned rows, with the direction of elongation of said openings being disposed in the direction of elongation of said container.

13. The container according to claim 10 wherein said measuring slide is provided with side arms extending over sides of said container for guiding said measuring slide in slidable relation along said container.

14. The container according to claim 13 wherein said measuring slide is removable.

15. The container according to claim 13 wherein said foraminous side comprises a substantially flat bottom of said container, said measuring slide further including inwardly directed tabs extending underneath said container for holding said measuring slide to said container, said tabs extending inwardly insufficiently far to cover said small openings.

16. The container according to claim 15 wherein said side including an opening and a closure comprises the top of said container provided with a rectangular lid, said lid being transparent and said cross member of said measuring slide extending thereover.

17. The method of determining the sharpness of a saw chain comprising the steps of:

operating said saw chain on a chain saw for cutting wood and collecting a quantity of wood chips produced as the result of such operation, screening said wood chips through a foraminous body of predetermined aperture size for passing at least a proportion of chips as produced by dull saw teeth while retaining properly sized chips as produced by sharp saw teeth, and measuring the relative quantity of wood chips passed and retained, for determining the overall sharpness of said saw chain.

18. The method of determining the sharpness of a saw chain comprising the steps of:

operating said saw chain on a chain saw for cutting wood and collecting a quantity of wood chips produced as a result of such operation, placing said wood chips in a perforated container and closing said container except for said perforations, shaking said container for shaking a proportion of wood chips through container perforations of predetermined size when said wood chips are produced by dull saw teeth, while otherwise retaining within said container properly sized wood chips produced by sharper saw teeth, and measuring the quantity of wood chips remaining within said container for determining the overall sharpness of said saw chain.

19. The method according to claim 18 wherein said measuring the quantity of wood chips remaining within said container comprises placing a movable slide in juxtaposition with said container adjacent the level of wood chips in said container prior to shaking thereof so the reduction in level after shaking can be ascertained by comparison with the position of said slide.

20. The method according to claim 19 including turning said container on end for establishing a level of wood chips therewithin before placing said movable slide adjacent said level.

* * * * *